United States Patent [19]

Wolf

[11] Patent Number: 4,547,215
[45] Date of Patent: Oct. 15, 1985

[54] HERBICIDAL SULFONAMIDES

[75] Inventor: Anthony D. Wolf, Elkton, Md.

[73] Assignee: E. I. Du Pont de Nemours and Company, Wilmington, Del.

[21] Appl. No.: 528,607

[22] Filed: Sep. 6, 1983

Related U.S. Application Data

[63] Continuation-in-part of Ser. No. 392,364, Mar. 24, 1983, abandoned.

[51] Int. Cl.$^4$ .................... C07D 239/69; A01N 47/36
[52] U.S. Cl. ...................................... 71/92; 544/321; 544/354

[58] Field of Search .................... 71/92; 544/321, 332, 544/354

[56] References Cited

U.S. PATENT DOCUMENTS 4,348,220  9/1982  Schwing ............................ 71/92
4,394,506  7/1983  Levitt ............................. 544/321

Primary Examiner—Robert Gerstl

[57] ABSTRACT

This invention relates to novel sulfonamides, agriculturally suitable compositions containing them and their method-of-use as selective pre-emergent or post-emergent herbicides.

18 Claims, No Drawings

HERBICIDAL SULFONAMIDES

RELATED APPLICATIONS

This application is a continuation-in-part of my co-pending application U.S. Ser. No. 392,364, filed Mar. 24, 1983 now abandoned.

BACKGROUND OF THE INVENTION

This invention relates to novel N-(heterocyclicaminocarbonyl)arylsulfonamides in which the aryl radical is substituted with a carboxyl radical. The compounds of this invention and their agriculturally suitable salts, are useful as agricultural chemicals, herbicides which may be selective and regulate growth.

In EPO Publication No. 7,687, there is disclosed herbicidal compounds of the general formula within the broad generic scope.

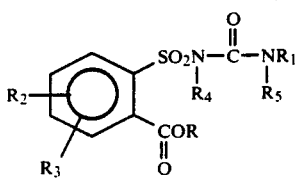

wherein
R may be $C_1$-$C_{12}$ alkyl;
$R_2$ and $R_3$ may be hydrogen, as may $R_4$ and $R_5$;
$R_1$ may be

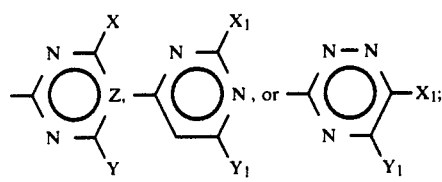

$R_2$ is H, Cl, Br, F, $C_1$-$C_3$ alkyl, $-NO_2$, $-SO_2CH_3$, $-OCH_3$, $-SCH_3$, $-CF_3$, $-N(CH_3)_2$, $-NH_2$ or $-CN$;
$R_3$ is H, Cl, Br, F or $CH_3$;
$R_4$ is H or $-CH_3$;
$R_5$ is H, $-CH_3$ or $-OCH_3$;
Z is CH or N;
X is H, Cl, $-CH_3$, $-OCH_3$, $-OCH_2CH_3$ or $-OCH_2CH_2OCH_3$;
Y is H; Cl; $C_1$-$C_4$ alkyl; $C_1$-$C_4$ alkyl substituted with $-OCH_3$, $-OC_2H_5$, $-CN$, $-CO_2CH_3$, $-CO_2C_2H_5$, or 1 to 3 atoms of F, Cl, Br; $C_3$-$C_4$ alkenyl; $-CH_2C\equiv CR_{13}$ where $R_{13}$ is H, $-CH_3$, $-CH_2Cl$; $-A-(CH_2)_{n'}A_1-(C_1$-$C_3$ alkyl), and n', A and $A_1$ are as previously defined.

The presence of undesired vegetation causes substantial damage to useful crops, especially agricultural products that satisfy man's basic food and fiber needs, such as rice, corn and soybeans. Compounds such as the ones indicated above, are extremely effective for killing or inhibiting the growth of undesired vegetation; such materials are commonly referred to as herbicides. The need still exists for more effective herbicides.

SUMMARY OF THE INVENTION

This invention relates to novel compounds of Formula I, agriculturally suitable compositions containing them and their method-of-use as selective preemergent or post-emergent herbicides.

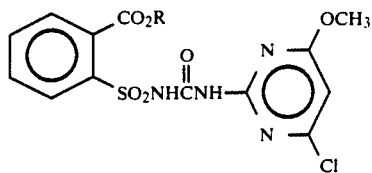

wherein R is $C_2H_5$ or $CH(CH_3)_2$; and their agriculturally suitable salts.

This invention also relates to herbicidally effective combinations of compounds of Formula I with compounds of Formula II

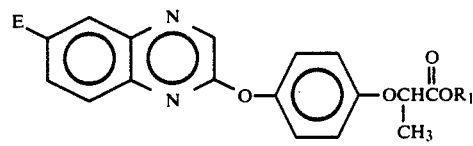

wherein
E is H, Cl, Br, F or $CF_3$; and
$R_1$ is $C_1$-$C_4$ alkyl or $CH_2CH_2OCH_2CH_2OCH_2CH_3$.

This invention also relates to herbicidally effective combinations of compounds of Formula I with the compound of Formula III

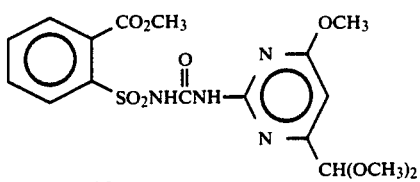

Specifically preferred are:
2-[[(4-chloro-6-methoxypyrimidin-2-yl)aminocarbonyl]aminosulfonyl]benzoic acid ethyl ester, m.p. 198°-201°; and
2-[[(4-chloro-6-methoxypyrimidin-2-yl)aminocarbonyl]aminosulfonyl]benzoic acid isopropyl ester, m.p. 185°-187°.

DETAILED DESCRIPTION OF THE INVENTION

Compounds of Formula I are prepared by the procedure of Equation 1. This procedure is well known in the art.

EQUATION 1

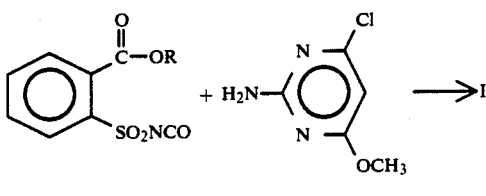

a  b

For details, one may refer to EPO Publication No. 0007687 and U.S. Pat. No. 4,169,719 which are herein incorporated by reference.

Sulfonyl isocyanates of Formula a are also known in the art. For example, U.S. Pat. No. 4,305,884 teaches the preparation of these compounds.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkai metal or quaternary amine salt) through a column packed with a cation exchange resin containing the cation to be exchanged for that of the original salt and the desired product is eluted from the column. This method is particularly useful when the desired salt is water-soluble.

Acid addition salts, useful in this invention, can be obtained by reacting a compound of Formula I with a suitable acid, e.g., p-toluenesulfonic acid, trichloroacetic acid or the like.

The compounds of this invention and their preparation are further illustrated by the following examples wherein temperatures are given in degrees centigrade and parts are by weight unless otherwise designated.

EXAMPLE 1

2-Amino-4-chloro-6-methoxypyrimidine 16.4 g 2-amino-4,6-dichloropyrimidine (purchased from Aldrich Chemical Co., Milwaukee, WI 53201) was added to 200 ml of $CH_3OH$. The mixture was cooled to 10° with an ice bath and 5.4 g of $NaOCH_3$ was added in portions while maintaining the temperature. The reaction mixture was allowed to warm to ambient temperature and then heated to reflux for two hours. The reaction mixture was then allowed to cool to ambient temperature and it was stirred overnight. A yellow solid was filtered and recrystallized from butyl chloride. The resulting solid was chromatographed on a dry column of silica, and eluted with 40% EtOAchexane. The resulting yellow solid was further purified by recrystallization from butyl chloride. 9.4 g of product with m.p. 163°-166° was obtained.

EXAMPLE 2

2-[[(4-chloro-6-methoxypyrimidin-2-yl)aminocarbonyl]aminosulfonyl]benzoic acid ethyl ester To 1.0 g of 2-amino-4-chloro-6-methoxypyrimidine suspended in 25 ml of dry $CH_2Cl_2$ was added 1.53 g of ethyl 2-(isocyanatosulfonyl)benzoate (prepared by procedures taught in U.S. Pat. No. 4,305,884). The reaction mixture was stirred at ambient temperature for three days. The solvent was stripped and the product was recrystallized from butyl chloride to give a white solid with m.p. 198°-201°.

Using procedures analogous to Example 2, 2-[[(4-chloro-6-methoxyprimidin-2-yl)aminocarbonyl]aminosulfonyl]benzoic acid isopropyl ester may be prepared.

The compounds of this invention may be used in combination with other commercial herbicides. They are particularly useful in combination with the following herbicides.

| Common Name | Chemical Name |
| --- | --- |
| amitrole | 3-amino-s-triazole |
| atrazine | 2-chloro-4-(ethylamino)-6-(isopropylamino)-s-triazine |
| barban | 4-chloro-2-butynyl m-chlorocarbanilate |
| benzoylprop | N—benzoyl-N—(3,4-dichlorophenyl)-DL-alaine |
| bromacil | 5-bromo-3-sec-butyl-6-methyluracil |
| bromoxynil | 3,5-dibromo-4-hydroxybenzonitrile |
| butylate | S—ethyl-diisobutylthiocarbamate |
| chlortoluron | N'—(3-chloro-4-methylphenyl-N',N'—dimethylurea |
| cyanazine | 2-[[4-chloro-6-(ethylamino)-s-triazin-2-yl]amino]-2-methylpropionitrile |
| diallate | S—(2,3-dichloroallyl)diisopropylthiocarbamate |
| dicamba | 3,6-dichloro-o-anisic acid |
| dichloroprop | 2-(2,4-dichlorophenoxy)propionic acid |
| diclofop | 2-[4-(2,4-dichlorophenoxy)phenoxy]-propanoic acid |
| difenzoquat | 1,2-dimethyl-3,5-diphenyl-1H—pyrazolium |
| dinoseb | 2-sec-butyl-4,6-dinitrophenol |
| diuron | 3-(3,4-dichlorophenyl)-1,1-dimethylurea |
| EPTC | S—ethyl-dipropylthiocarbamate |
| flamprop | N—benzoyl-N—(3-chloro-4-fluorophenyl)-DL-alanine |
| fluchloralin | N—(2-chloroethyl)-2,6-dinitro-N—propyl-4-trifluoromethyl)aniline |
| fluometuron | 1,1-dimethyl-3-($\alpha,\alpha,\alpha$-trifluoro-m-tolyl)-urea |
| fomesafen | 5-(2-chloro-4-trifluoromethylphenoxy)-N—methylsulfonyl-2-nitrobenzamide |
| fosamine | ethyl hydrogen (aminocarbonyl)phosphonate |
| glyphosate | N—(phosphonomethyl)glycine |
| hexazinone | 3-cyclohexyl-6-(dimethylamino)-1-methyl-1,3,5-triazine-2,4(1H,3H)—dione |
| ioxynil | 4-hydroxy-3,5-diiodobenzonitrile |
| isoproturon | N—(4-isopropylphenyl)-N',N'—dimethylurea |
| lenacil | 3-cyclohexyl-6,7-dihydro-1H—cyclopenta-pyrimidine-2,4(3H,5H)—dione |
| MCPA | [(4-chloro-o-tolyl)oxy]acetic acid |
| MCPB | 4-[(4-chloro-o-tolyl)oxy]propionic acid |
| mefluidide | N—[2,4-dimethyl-5-[[(trifluoromethyl)-sulfonyl]amino]phenyl]acetamide |
| methabenzthiazuron | 1,3-dimethyl-3-(2-benzothiazolyl)urea |
| methoxuron | N'—(3-chloro-4-methoxyphenyl)N,N—dimethylurea |
| MSMA | monosodium methanearsonate |
| neburon | 1-butyl-3-(3,4-dichlorophenyl)-1-methyl-urea |
| oryzalin | 3,4-dinitro-N,N—dipropylsulfanilamide |
| paraquat | 1,1'-dimethyl-4,4'-bipyridinium ion |
| profluralin | N—(cyclopropylmethyl)-$\alpha,\alpha,\alpha$-trifluoro-2,6-dinitro-N—propyl-p-toluidine |
| propanil | 3',4'-dichloropropionalide |
| siduron | 1-(2-methylcyclohexyl)-3-phenylurea |
| supriox | 2-[1-(2,5-dimethylphenyl)ethylsulfonyl]-pyridine-N—oxide |
| terbacil | 3-tert-butyl-5-chloro-6-methyluracil |
| triallate | S—(2,3,3-trichloroallyl)diisopropylthiocarbamate |
| 2,4-D | (2,4-dichlorophenoxy)acetic acid |
| 2,4-DB | 4-(2,4-dichlorophenoxy)butyric acid |
| | 3,4-diaryl-4-cyanobutyrates |
| | 4-(6-chloroquinoxalinyl-2-oxy)phenoxy-propionate $C_1$-$C_5$ alkyl esters, such as methyl ester, butyl ester, ethyl ester, pentyl ester |
| | ethoxyethoxyethyl 4-(6-chloroquinoxalin-yl-2-oxy)phenoxypropionate |
| | propargyl 2-[4-(3,5-dichloropyridin-2-yloxy)phenoxy]propanoate |

| Common Name | Chemical Name |
| --- | --- |
| | methyl 2-[4-(3-chloro-5-trifluoromethyl-pyridin-2-yloxy)phenoxy]propanoate |
| oxyfluorfen | 2-chloro-1-(3-ethoxy-4-nitrophenoxy)-4-(trifluoromethyl)benzene |
| norflurazon | 4-chloro-5-(methylamino)-2-[(3-(trifluoro)phenyl]-3(2H)—pyridazinone |
| vernolate | S—propyl dipropylthiocarbamate |
| | ethyl 5-[2-chloro-4-(trifluoromethyl)-phenoxy]-2-nitrobenzoic acid |

The compounds of this invention may particularly be useful in combination with the following herbicides for use as pre- or post-emergent treatments for control of weeds in soybeans:

| Common Name | Tradename | Chemical Name |
| --- | --- | --- |
| acifluorfen | Blazer ® | 5-[2-chloro-4-(trifluoromethyl)phenoxy]-2-nitrobenzoic acid |
| alachlor | Lasso ® | 2-chloro-2',6'-diethyl-N—(methoxymethyl)acetanilide |
| bentazon | Basagran ® | 3-isopropyl-1H—2,1,3-benzothiadiazin-4(3H)—one 2,2-dioxide |
| chloramben | Amiben ® | 3-amino-2,5-dichlorobenzoic acid |
| fluazifop-butyl | Fusilade ® | butyl 2-[4-[5-(trifluoromethyl)-2-pyridinyl-oxy]phenoxy]propanoate |
| linuron | Lorox ® | 3-(3,4-dichlorophenyl)-1-methoxy-1-methylurea |
| metolachlor | Dual ® | 2-chloro-N—(2-ethyl-6-methylphenyl)-N—(2-methoxy-1-methylethyl)-acetamide |
| metribuzin | Lexone ® | 4-amino-6-tert-butyl-3-(methylthio)-as-triazin-5(4H)one |
| pendimethalin | Prowl ® | N—(1-ethylpropyl)-3,4-dimethyl-2,6-dinitrobenzeneamine |
| sethoxydim | Poast ® | 2-[1-(ethoxyimino)butyl]-5-[2-(ethylthio)-propyl]-3-hydroxy-2-cyclohexene-1-one |
| trifluralin | Treflan ® | α,α,α-trifluoro-2,6-dinitro-N,N—dipropyl-p-toluidine |
| AC 252,214 | — | 2-(4,5-dihydro-4-methyl-4-(1-methylethyl)-5-oxo-1H—imidazol-2-yl)-3-quinolinecarboxylic acid |
| FMC 57020 | — | 2-(2'-chlorophenyl)-methyl-4,4-dimethyl-3-isoxazolidinone |
| fomesafen | Flex ® | 5-(2-chloro-4-trifluoromethylphenoxy)-N—methylsulfonyl-2-nitrobenzamide |
| lactofen | — | 1'-(carboethoxy)ethyl-5-(2-chloro-4-(trifluoromethyl)phenoxy)-2-nitrobenzoate |
| DOWCO 453 ME | | 2-(4-(3-chloro-5-trifluoromethylpyridin-2-yloxy)phenoxy)propanoic acid, methyl ester |
| fenoxaprop ethyl | Whip ® | ethyl 2-(4-(6-chloro-2-benzoxazolyloxy)phenoxy)propanoate |
| CGA 82725 | Topik ® | 2-(4-(3,5-dichloropyridin-2-yloxy)phenoxypropanoic acid, propynyl ester |

A particularly preferred mixture would be an effective amount of a compound of Formula I and an effective amount of a compound of Formula II below:

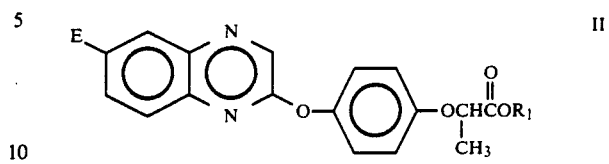

Most preferred would be a mixture with a compound of Formula II wherein Z is Cl and R is $CH_2CH_3$.

Ratios in the mixture should be 3 to 48% by weight of a compound of Formula I and 52 to 97% by weight of a compound of Formula II. Preferably 6 to 20% of a compound of Formula I and 80 to 94% of a compound of Formula II.

The compounds of Formula II may be prepared by the process disclosed in EPO Application No. 81,302,801.6, published Dec. 30, 1981 and EPO Application No. 82,306,769.9, published June 29, 1983.

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE I

| | Active Ingredient | Weight Percent* | |
| --- | --- | --- | --- |
| | | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredients can, of coruse, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950.

Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration technique. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 3

Wettable Powder

| | |
|---|---|
| 2-[[(4-chloro-6-methoxypyrimidin-2-yl)aminocarbonyl]aminosulfonyl]benzoic acid ethyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 4

Low Strength Granule

| | |
|---|---|
| 2-[[(4-chloro-6-methoxypyrimidin-2-yl)aminocarbonyl]aminosulfonyl]benzoic acid ethyl ester | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 5

Aqueous Suspension

| | |
|---|---|
| 2-[[(4-chloro-6-methoxypyrimidin-2-yl)aminocarbonyl]aminosulfonyl]benzoic acid isopropyl ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 6

Granule

| | |
|---|---|
| 2-[[(4-chloro-6-methoxypyrimidin-2-yl)aminocarbonyl]aminosulfonyl]benzoic acid isopropyl ester | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 7

High Strength Concentrate

| | |
|---|---|
| 2-[[(4-chloro-6-methoxypyrimidin-2-yl)aminocarbonyl]aminosulfonyl]benzoic acid ethyl ester | 99% |
| silica aerogel | 0.5% |
| synthetic amorphous silica | 0.5% |

The ingredients are blended and ground in a hammermill to produce a material essentially all passing a U.S.S. No. 50 screen (0.3 mm opening). The concentrate may be formulated further if necessary.

EXAMPLE 8

Wettable Powder

| | |
|---|---|
| 2-[[(4-chloro-6-methoxypyrimidin-2-yl)aminocarbonyl]aminosulfonyl]benzoic acid isopropyl ester | 90% |
| dioctyl sodium sulfosuccinate | 0.1% |

| | |
|---|---|
| -continued | |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 9

Wettable Powder

| | |
|---|---|
| 2-[[(4-chloro-6-methoxypyrimidin-2-yl)amino-carbonyl]aminosulfonyl]benzoic acid isopropyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 10

Wettable Powder

| | |
|---|---|
| 2-[[(4-chloro-6-methoxypyrimidin-2-yl)amino-carbonyl]aminosulfonyl]benzoic acid ethyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 11

Granule

| | |
|---|---|
| Wettable Powder of Example 10 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 12

Extruded Pellet

| | |
|---|---|
| 2-[[(4-chloro-6-methoxypyrimidin-2-yl)amino-carbonyl]aminosulfonyl]benzoic acid ethyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 13

Oil Suspension

| | |
|---|---|
| 2-[[(4-chloro-6-methoxypyrimidin-2-yl)amino-carbonyl]aminosulfonyl]benzoic acid isopropyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 14

Wettable Powder

| | |
|---|---|
| 2-[[(4-chloro-6-methoxypyrimidin-2-yl)amino-carbonyl]aminosulfonyl]benzoic acid ethyl ester | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 15

Oil Suspension

| | |
|---|---|
| 2-[[(4-chloro-6-methoxypyrimidin-2-yl)amino-carbonyl]aminosulfonyl]benzoic acid ethyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 16

Dust

| | |
|---|---|
| 2-[[(4-chloro-6-methoxypyrimidin-2-yl)amino-carbonyl]aminosulfonyl]benzoic acid ethyl ester | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 17

Emulsifiable Concentrate

| | |
|---|---|
| 2-[[(4-chloro-6-methoxypyrimidin-2-yl)aminocarbonyl]aminosulfonyl]benzoic acid ethyl ester | 20% |
| chlorobenzene | 74% |
| sorbitan monostearate and polyoxyethylene condensates thereof | 6% |

The ingredients are combined and stirred to produce a solution which can be emulsified in water for application.

UTILITY

The compounds of the present invention have high herbicidal properties. They have utility for broadspectrum pre- and/or post-emergence weed control, in particular selective weed control in soybeans.

The rates of application for the compounds of the invention are determined by a number of factors, including the types of weeds to be controlled, weather and climate, formulations selected, mode of application, amount of foliage present, etc. In general terms, the subject compounds should be applied at levels of around 0.002 to 1 kg/ha, the lower rates being suggested for use on lighter soils and/or those having a low organic matter content, or for situations where only short-term persistence is required.

The compounds of the invention may be used in combination with any other commercial herbicide, examples of which are those of the triazine, triazole, uracil, urea, amide, diphenylether, carbamate and bipyridylium types.

As mentioned previously, compounds of this invention may also be used in combination with herbicides such as those of Formula II. Compound 3 is representative of this class of compounds, and may be used at rates of 0.035 to 1 kg/ha depending upon the above factors. Such combinations or split applications may be useful in obtaining both grass and broadleaf weed control in soybeans.

The herbicidal properties of the subject compounds were discovered in a number of greenhouse tests. The test procedures and results follow.

TEST A

Seeds of crabgrass (Digitaria sp.), barnyardgrass (*Echinochloa crusgalli*), wild oats (*Avena fatua*), sicklepod (*Cassia obtusifolia*), morningglory (Ipomoea sp.), cocklebur (*Xanthium pensylvanicum*), sorghum, corn, soybean, sugar beet, rice, wheat and purple nutsedge (*Cyperus rotundus*) tubers were planted and treated pre-emergence with the test chemicals dissolved in a non-phytotoxic solvent. At the same time, these crop and weed species, along with cotton and bush bean, were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
D=defoliation;
E=emergence inhibition;
G=growth retardation;
H=formative effects;
U=unusual pigmentation; and
6Y=abscised buds or flowers.

The data indicate the high herbicidal activity of the compounds of the invention and their utility for selective pre-emergence weed control in soybeans.

Compounds

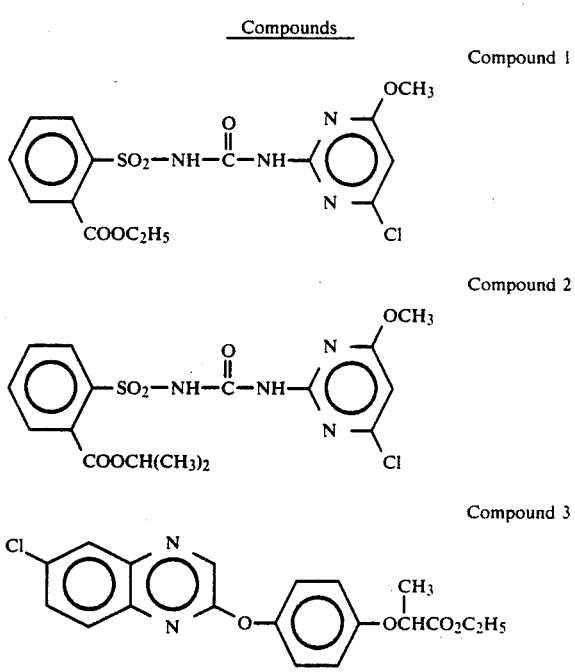

Compound 1

Compound 2

Compound 3

TABLE A

| Rate kg/ha | Cmpd. 1 0.05 | Cmpd. 2 0.05 |
|---|---|---|
| POST-EMERGENCE | | |
| Bush bean | 9C | 9C |
| Cotton | 2C,9G | 3C,3H,9G |
| Morningglory | 10C | 9C |
| Cocklebur | 10C | 9C |
| Sicklepod | 9C | 9C |
| Nutsedge | 9C | 9G |
| Crabgrass | 2C,4G | 2C,5G |
| Barnyardgrass | 5C,9H | 3C,9H |
| Wild Oats | 6C,9G | 8G |
| Wheat | 6C,9G | 2C,9G |
| Corn | 5U,9C | 2C,8H |
| Soybean | 4C,9G | 2C,6G |
| Rice | 5C,9G | 5C,9G |
| Sorghum | 5C,9G | 3C,9G |
| Sugar beet | 5C,9G | 4C,9G |
| PRE-EMERGENCE | | |
| Morningglory | 9C | 9C |
| Cocklebur | — | 9H |
| Sicklepod | 9G | 8G |
| Nutsedge | 10E | 10E |
| Crabgrass | 0 | 0 |
| Barnyardgrass | 2C,9H | 4C,9H |
| Wild Oats | 2C,8G | 2C,6G |
| Wheat | 9H | 8G |
| Corn | 2C,9G | 1C,9G |
| Soybean | 0 | 1C |
| Rice | 10E | 10E |
| Sorghum | 7C,9H | 2C,9H |
| Sugar beet | 10E | 10E |

TEST B

Two plastic bulb pans were filled with fertilized and limed Woodstown sandy loam. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with the test compounds of the invention.

Twenty-eight days after treatment, the plants were evaluated and visually rated for response to the chemical treatments utilizing the rating system described previously for Test A. The data are summarized in Table B. Note that the compounds are useful as pre-emergence treatments for weed control in soybeans.

cm diameter by 13 cm deep): soybeans, cotton, alfalfa, corn, rice, wheat, sorghum, velvetleaf (*Abutilon theophrasti*), sesbania (*Sesbania exaltata*), sicklepod (*Cassia obtusifolia*), morningglory (*Ipomoea hederacea*), jimsonweed (*Datura stramonium*), cocklebur (*Xanthium pensylvaicum*), crabgrass (Digitaria sp.), nutsedge (*Cyperus rotundus*), barnyardgrass (*Echinochloa crusgalli*), giant foxtail (*Setaria faberii*) and wild oats (*Avena fatua*). The following species were grown in soil in a paper cup (12 cm diameter by 13 cm deep): sunflower, sugar beets, and mustard. All plants were sprayed approximately 14 days after planting. Additional plant species are sometimes added to this standard test in order to evaluate unusual selectivity.

The compounds tested by this procedure are useful for the post-emergence control of weeds in soybeans.

TABLE C

| | Over-the-Top Soil/Foliage Treatment | | | | | |
|---|---|---|---|---|---|---|
| | Compound 1 | | | Compound 2 | | |
| Rate kg/ha | .004 | .016 | .063 | .004 | .016 | .063 |
| Soybeans | 0 | 5G | 9G | 0 | 7G | 8G,6C |
| Velvetleaf | 9G,4C | 10C | 10C | 9G | 10C | 10C |
| Sesbania | 10C | 10C | 10C | 10C | 10C | 10C |
| Sicklepod | 7G | 10C | 10G,4C | 6G,4C | 10C | 10G,4C |
| Cotton | 8G | 10C | 10C | 10C | 10C | 10C |
| Morningglory | 9G,2C | 10C | 9G,9C | 10C | 9G,8C | 10C |
| Alfalfa | 5G | 10C | 9G,8C | 10C | 8G,2C | 10C |
| Jimsonweed | 8G | 9G,2C | 9G | 8G | 10C | 10C |

TABLE B

| | PRE-EMERGENCE ON WOODSTOWN SANDY LOAM | | | | | | | | | | | | |
|---|---|---|---|---|---|---|---|---|---|---|---|---|---|
| | Compound 1 | | | | | | Compound 2 | | | | | | |
| Rate kg/ha | 0.00175 | 0.0035 | 0.015 | 0.030 | 0.060 | 0.500 | 0.00175 | 0.0035 | 0.015 | 0.030 | 0.060 | 0.120 | 0.500 |
| Crabgrass | 5G | 5G | 3G | 6G | 6G | 9G | 2G | 2G | 0 | 2G | 3G | 5G | 8G |
| Barnyardgrass | 6G | 6G | 9G | 9G,9C | 9G,9C | 10C | 4G | 5G | 6G | 7G | 8G | 8G | 9G,9C |
| Sorghum | 7G | 9G,9C | 10C | 10C | 10C | 10C | 5G | 7G | 10C | 10C | 10C | 10C | 10C |
| Wild Oats | 3G | 4G | 8G | 8G,3C | 8G,5C | 9G,9C | 2G | 3G | 4G | 5G | 7G | 7G | 9G |
| Johnsongrass | 0 | 0 | 8G | 8G | 8G | 9G,9C | 0 | 0 | 7G | 7G | 8G | 8G | 9G,9C |
| Dallisgrass | 0 | 2G | 5G | 7G | 8G | 9G | 0 | 0 | 4G | 5G | 5G | 6G | 9G |
| Giant foxtail | 0 | 2G | 6G | 7G | 7G | 9G | 2G | 2G | 4G | 5G | 8G | 9G | 9G |
| Ky. bluegrass | 0 | 2G | 9G | 9G | 9G,9C | 10C | 2G | 5G | 8G | 9G | 9G | 9G | 10C |
| Cheatgrass | 8G | 9G | 9G,9C | 10C | 10C | 10C | 7G | 8G | 9G,9C | 9G,9C | 9G,9C | 10C | 10C |
| Sugar beets | 9G | 9G | 10C | 10C | 10C | 10C | 9G | 9G | 9G | 9G | 9G,9C | 10C | 10C |
| Corn | 2G | 3G | 6G | 8G,5H | 8G,7H | 10C | 0 | 2G | 4G | 3G | 6G | 8G,5H | 10C |
| Mustard | 9G | 9G | 9G,9C | 9G,9C | 10C | 10C | 9G | 9G | 9G,9C | 9G,9C | 10C | 10C | 10C |
| Cocklebur | 7G | 8G | 9G,3H | 9G,5H | 9G,7H | 9G,9C | 7G | 8G | 9G,5H | 9G,5H | 9G,7H | 9G,7H | 9G,9C |
| Pigweed | — | — | — | — | — | — | — | — | — | — | — | — | — |
| Nutsedge | 10C | 10C | 10C | 10C | 10C | 10C | 8G | 9G | 10C | 10C | 10C | 10C | 10C |
| Cotton | 8G | 8G | 9G | 9G | 9G | 10C | 6G | 8G | 8G | 8G | 8G | 9G | 9G,9C |
| Morningglory | 5G | 7G | 9G | 9G | 9G | 9G,9C | 5G | 7G | 9G | 9G | 9G | 9G | 9G,9C |
| Sicklepod | 4G | 6G | 8G | 9G | 9G | 9G,9C | 0 | 4G | 2G | 5G | 8G | 8G | 9G |
| Teaweed | 0 | 4G | 8G | 9G | 9G | 9G,9C | 0 | 0 | 8G | 8G | 9G | 9G | 9G |
| Velvetleaf | 4G | 7G | 8G | 9G | 9G | 9G,9C | 0 | 5G | 7G | 8G | 9G | 9G | 9G,9C |
| Jimsonweed | 7G | 9G,9C | 9G,9C | 9G,9C | 9G,9C | 9G,9C | 6G | 8G | 9G | 9G | 9G,9C | 9G,9C | 9G,9C |
| Soybean | 0 | 0 | 2G | 2G | 3G | 7G | 0 | 0 | 0 | 0 | 2G | 2G | 6G |
| Rice | 9G | 10C | 10C | 10C | 10C | 10C | 9G | 9G | 10C | 10C | 10C | 10C | 10C |
| Wheat | 4G | 7G | 3G | 6G | 8G | 9G | 4G | 6G | 5G | 4G | 5G | 6G | 8G |

TEST C

The test chemicals, dissolved in a non-phytotoxic solvent, were applied in an overall spray to the foliage and surrounding soil of selected plant species. One day after treatment, plants were observed for rapid burn injury. Approximately fourteen days after treatment, all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25

| Cocklebur | 9G,1H | 8G,1H | 9G | — | 9G | 10C |
|---|---|---|---|---|---|---|
| Sunflower | 10C | 10C | 10C | 9G,9C | 10C | 10C |
| Mustard | 9G,5C | 10C | 10C | 9G,6C | 9G,6C | 9G,4C |
| Sugar beets | 10C | 10C | 10C | 9G | 10C | 10C |
| Corn | 2G,2C | 5G,1U | 7G | 1C | 2G,2C | 5G,2H |
| Crabgrass | 0 | 0 | 0 | 0 | 2G | 0 |
| Rice | 8G,2C | 9G,8C | 9G,8C | 6G | 9G,7C | 9G,4C |
| Nutsedge | 9G | 8G | 8G,6C | 7G | 7G,6C | 7G |
| Barnyardgrass | 6G | 8G,6C | 9G,6C | 5G | 7G | 8G,6C |
| Wheat | 4G | 8G | 9G | 0 | 6G | 8G |
| Giant foxtail | 6G | 7G | 8G | 3G | 6G | 9G |
| Wild Oats | 2G | 7G | 8G | 0 | 4G | 7G |
| Sorghum | 6G | 8G,1U | 9G,2U | 7G | 7G,2U | 7G,2U |
| Johnsongrass | 5G | 8G,1U | 8G,1U | 5G | 7G | 7G,4U |
| Field | 0 | 8G | 8G | 6G | 4G | 8G |

TABLE C-continued

| | Over-the-Top Soil/Foliage Treatment | | | | | |
|---|---|---|---|---|---|---|
| | Compound 1 | | | Compound 2 | | |
| Rate kg/ha | .004 | .016 | .063 | .004 | .016 | .063 |
| Bindweed | | | | | | |

TEST D

Four inch round pots were filled with Woodstown soil and various weed seeds were sown in separate pots. The pots containing the seeds were placed in the greenhouse and watered as needed for good plant growth. In addition, they were fertilized once with 10-10-10 Peter's solution. After about 3 weeks depending on species, when the plants were in the 4-6 true leaf stage, they were sprayed with solutions of Compound 1, Compound 3 or both using a track sprayer calibrated to deliver 60 g.p.a. of the spray solution containing 0.1% X-77 surfactant. The plants were replaced in the greenhouse and watered as needed for optimum growth for about 3 weeks. They were then evaluated for percent weed control where 0=no control and 100=complete kill. The following weeds were in the test. Barnyardgrass (*Echinochloa crusgalli*), giant foxtail (*Setaria faberi*), velvetleaf (*Abutilon theophrasti*), hemp sesbania (*Sesbania exaltata*), sicklepod (*Cassia Obtusifolia*), kochia (*Kochia scoparia*) and Russian thistle (*Salsola kali*). The data are summarized in Table D.

TABLE D

| | Rate (kg a.i./ha) | | | | |
|---|---|---|---|---|---|
| Test 1 | | | | | |
| Compound 3 | 1/16 | 1/32 | 1/64 | 1/128 | 1/256 |
| Compound 2 | 1/64 | 1/128 | 1/256 | 1/512 | 1/1024 |
| Barnyardgrass | 95 | 95 | 90 | 70 | 50 |
| Giant Foxtail | 100 | 100 | 99 | 80 | 50 |
| Velvetleaf | 100 | 99 | 90 | 90 | 90 |
| Hemp sesbania | 100 | 100 | 100 | 100 | 90 |
| Sicklepod | 95 | 95 | 95 | 60 | 60 |
| Kochia | 30 | 30 | 0 | 0 | 0 |
| Russian thistle | 20 | 20 | 0 | 0 | 0 |
| Test 2 | | | | | |
| Compound 3 | 1/16 | 1/32 | 1/64 | 1/128 | 1/256 |
| Compound 2 | 1/64 | 1/128 | 1/256 | 1/512 | 1/1024 |
| Barnyardgrass | 95 | 90 | 80 | 80 | 50 |
| Giant Foxtail | 99 | 99 | 90 | 70 | 50 |
| Velvetleaf | 100 | 100 | 100 | 50 | 50 |
| Hemp sesbania | 100 | 100 | 100 | 90 | 100 |
| Sicklepod | 95 | 100 | 85 | 40 | 40 |
| Kochia | 60 | 50 | 30 | 0 | 0 |
| Russian thistle | 70 | 50 | 0 | 0 | 0 |
| Test 3 | | | | | |
| Compound 3 | 0 | 0 | 0 | 0 | 0 |
| Compound 2 | 1/64 | 1/128 | 1/256 | 1/512 | 1/1024 |
| Barnyardgrass | 0 | 0 | 0 | 0 | 0 |
| Giant Foxtail | 0 | 0 | 0 | 0 | 0 |
| Velvetleaf | 100 | 99 | 99 | 80 | 80 |
| Hemp sesbania | 100 | 100 | 100 | 90 | 85 |
| Sicklepod | 95 | 95 | 90 | 70 | 60 |
| Kochia | 50 | 40 | 20 | 0 | 0 |
| Russian thistle | 90 | 0 | 0 | 0 | 0 |
| Test 4 | | | | | |
| Compound 3 | 1/16 | 1/32 | 1/64 | 1/128 | 1/256 |
| Compound 2 | 0 | 0 | 0 | 0 | 0 |
| Barnyardgrass | 98 | 95 | 90 | 70 | 50 |
| Giant Foxtail | 100 | 100 | 100 | 80 | 60 |
| Velvetleaf | 0 | 0 | 0 | 0 | 0 |
| Hemp sesbania | 0 | 0 | 0 | 0 | 0 |
| Sicklepod | 0 | 0 | 0 | 0 | 0 |
| Kochia | 0 | 0 | 0 | 0 | 0 |
| Russian thistle | 0 | 0 | 0 | 0 | 0 |

What is claimed is:

1. A compound of the formula:

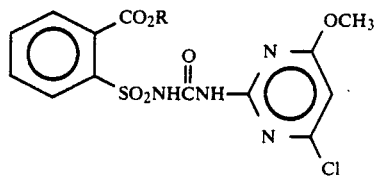

wherein R is $C_2H_5$ or $CH(CH_3)_2$; and their agriculturally suitable salts.

2. The compound of claim 1 which is 2-[[(4-chloro-6-methoxypyrimidin-2-yl)aminocarbonyl]aminosulfonyl]-benzoic acid ethyl ester.

3. The compound of claim 1 which is 2-[[(4-chloro-6-methoxypyrimidin-2-yl)aminocarbonyl]aminosulfonyl]-benzoic acid isopropyl ester.

4. A mixture of an herbicidally effective amount of a compound of claim 1 with an herbicidally effective amount of a compound of the formula:

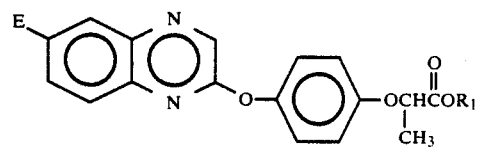

wherein
E is H, Cl, Br, F or $CF_3$; and
$R_1$ is $C_1$-$C_4$ alkyl or $CH_2CH_2OCH_2CH_2OCH_2CH_3$.

5. A mixture of an effective amount of the compound of claim 2 with an effective amount of the compound of claim 4 wherein E is Cl and R is $CH_2CH_3$.

6. A mixture of an effective amount of the compound of claim 2 with an effective amount of the compound of the formula:

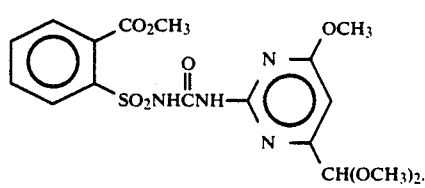

7. A composition suitable for controlling the growth of undesired vegetation which comprises an effective amount of a compound of claim 1 and at least one of the following: surfactant, solid or liquid diluent.

8. A composition suitable for controlling the growth of undesired vegetation which comprises an effective amount of the compound of claim 2 and at least one of the following: surfactant, solid or liquid diluent.

9. A composition suitable for controlling the growth of undesired vegetation which comprises an effective amount of the compound of claim 3 and at least one of the following: surfactant, solid or liquid diluent.

10. A mixture suitable for controlling the growth of undesired vegetation which comprises an effective amount of a mixture of claim 4 and at least one of the following: surfactant, solid or liquid diluent.

11. A mixture suitable for controlling the growth of undesired vegetation which comprises an effective amount of a mixture of claim 5 and at least one of the following: surfactant, solid or liquid diluent.

12. A method for controlling the growth of undesired vegetation which comprises applying to the locus to be protected an effective amount of a compound of claim 1.

13. A method for controlling the growth of undesired vegetation which comprises applying to the locus to be protected an effective amount of the compound of claim 2.

14. A method for controlling the growth of undesired vegetation which comprises applying to the locus to be protected an effective amount of the compound of claim 3.

15. A method for controlling the growth of undesired vegetation which comprises applying to the locus to be protected an effective amount of a mixture of claim 4.

16. A method for controlling the growth of undesired vegetation which comprises applying to the locus to be protected an effective amount of a mixture of claim 5.

17. A method for controlling the growth of undesired vegetation found growing in conjunction with soybeans which comprises applying to the locus to be protected an effective amount of the compound of claim 2.

18. A method for controlling the growth of undesired vegetation found growing in conjunction with soybeans which comprises applying to the locus to be protected an effective amount of the mixture of claim 5.

* * * * *